(12) United States Patent
Olstein

(10) Patent No.: US 7,960,164 B2
(45) Date of Patent: Jun. 14, 2011

(54) **SELECTIVE GROWTH MEDIUM FOR *LISTERIA* SPP**

(75) Inventor: Alan D. Olstein, Mendota Heights, MN (US)

(73) Assignee: Paradigm Diagnostics, Inc., St. Paul, MN (US)

( * ) Notice: Subject to any disclaimer, the term of this patent is extended or adjusted under 35 U.S.C. 154(b) by 987 days.

(21) Appl. No.: 10/597,909

(22) PCT Filed: Feb. 12, 2005

(86) PCT No.: PCT/US2005/004254
§ 371 (c)(1), (2), (4) Date: Jul. 25, 2007

(87) PCT Pub. No.: WO2005/079276
PCT Pub. Date: Sep. 1, 2005

(65) Prior Publication Data
US 2008/0020445 A1    Jan. 24, 2008

Related U.S. Application Data

(60) Provisional application No. 60/543,947, filed on Feb. 12, 2004.

(51) Int. Cl.
*C12N 1/20* (2006.01)
(52) U.S. Cl. .................................................. 435/253.6
(58) Field of Classification Search .................... None
See application file for complete search history.

(56) References Cited

OTHER PUBLICATIONS

Lee, et al., Improved *Listeria monocytogenes* selective agar, Applied and Environmental Microbiology, Nov. 1986, vol. 52, p. 1215-121.*
DIFCO Manual, 11 th edition, 1998, pp. 364-369 and 395-396.*
Neamatallah et al., An improved selective isolation medium for the recovery of *Listeria monocytogenes* from smoked fish, Letters in Applied Microbiology 2003, 36, 230-23.*
Al-Zoreky, N., et al., "Highly Selective Medium for Isolation of *Listeria monocytogenes* from Food," Applied and Environmental Microbiology, Oct. 1990, p. 3154-3157, vol. 56, No. 10.

Allona, A., et al., "Fosfomycin in Chronic Urinary Infections," Chemotherapy, 1977, p. 267-274, vol. 23 (Suppl. 1).
Bacardi, R., et al., "Treatment of Respiratory Infections with Fosfomycin," Chemotherapy, 1977, p. 343-347, vol. 23 (Suppl. 1).
Bannerman, E. S., et al., "A New Selective Medium for Isolating *Listeria* spp. from Heavily Contaminated Material," Applied and Environmental Microbiology, Jan. 1988, p. 165-167, vol. 54, No. 1.
Donnelly, C. W., et al., "Method for Flow Cytometric Detection of *Listeria monocytogenes* in Milk," Applied and Environmental Microbiology, Oct. 1986, p. 689-695, vol. 52, No. 4.
Fraser, J. A., et al., "Rapid Detection of *Listeria* spp. in Food and Environmental Samples by Esculin Hydrolysis," Journal of Food Protection, Oct. 1988, p. 762-765, vol. 51, No. 10.
Kestle, D. G., et al., "Clinical Pharmacology and In Vitro Activity of Phosphonomycin," Antimicrobial Agents and Chemotherapy, 1969, p. 332-337.
Lovett, J., et al., "*Listeria monocytogenes* in Raw Milk: Detection, Incidence, and Pathogenicity," Journal of Food Protection, Mar. 1987, p. 188-192, vol. 50, No. 3.
Peterson, M. E., et al., "Parameters for Control of *Listeria monocytogenes* in Smoked Fishery Products: Sodium Chloride and Packaging Method," Journal of Food Protection, Nov. 1993, p. 938-943.
Safdar, A., et al., "Antimicrobial Activities against 84 *Listeria monocytogenes* Isolates from Patients with Systemic Listeriosis at a Comprehensive Cancer Center (1955-1997)," Journal of Clinical Microbiology, Jan. 2003, p. 483-485, vol. 41, No. 1.
Soriano, F., et al., "Antimicrobial Susceptibilities of *Corynebacterium* Species and Other Non-Spore-Forming Gram-Positive Bacilli to 18 Antimicrobial Agents," Antimicrobial Agents and Chemotherapy, Jan. 1995, p. 208-214, vol. 39, No. 1.
Van Netten, P., et al., Liquid and solid selective differential media fro the detection and enumeration of *L. monocytogenes* and other *Listeria* spp., International Journal of Food Microbiology, 1989, p. 299-316, vol. 8.

* cited by examiner

*Primary Examiner* — Irene Marx
(74) *Attorney, Agent, or Firm* — Charles S. Sara, Esq.; Daniel A. Blasiole; Dewitt Ross & Stevens, S.C.

(57) ABSTRACT

The invention is a selective growth medium for investigating, isolating, counting and directly identifying pathogenic bacteria of the genus *Listeria*. The medium promotes the *Listeria* spp. while simultaneously inhibiting the growth of non-*Listeria* organisms. The medium does not produce a bacterial biomass contaminated with interfering fluorophores. The medium contains nitrofurantoin, esculin and lithium chloride and lacks acriflavin.

2 Claims, No Drawings

SELECTIVE GROWTH MEDIUM FOR *LISTERIA* SPP

CROSS-REFERENCE TO RELATED APPLICATION

This application claims priority under 35 USC §119(e) to U.S. Provisional Application Ser. No. 60/543,947, file Feb. 12, 2004, the entirety of which is incorporated herein.

REFERENCES AND INCORPORATION BY REFERENCE

Complete bibliographic citations for the references cited herein are contained in a section titled "REFERENCES," immediately preceding the claims. All of the documents listed in the "REFERENCES" section are incorporated herein.

FIELD OF THE INVENTION

The invention is directed to a *Listeria*-selective growth medium. The preferred embodiment of the medium comprises nitrofurantoin, esculin and lithium chloride, and is substantially devoid of acriflavin.

BACKGROUND OF THE INVENTION

Considerable microbiological research has been devoted to understanding the nutritional requirements and environmental conditions that promote selective growth of *Listeria* spp. Dependable selective culturing of *Listeria* spp. is becoming increasingly important in the food industry because of evolving federal and state regulations requiring more frequent monitoring of food-processing equipment and environments. *Listeria* spp. is considered to be a critical indicator of the effectiveness of industrial sanitation practices for two principle reasons: 1) organisms of the genus *Listeria* are ubiquitous; and 2) the species *Listeria monocytogenes* is pathogenic and thus a cause of concern for public health officials.

Among the bacteria of the genus *Listeria* spp., only the species *monocytogenes* is known to be pathogenic to humans. Other species of *Listeria* such as *L. ivanovii* are not generally pathogenic or are pathogenic only for animals. *L. monocytogenes* is a gram-positive, motile, aerobic and facultatively anaerobic bacterium which is ubiquitous in nature. It can cause various diseases in man including meningoencephalitis, low-grade septicemia, infectious mononucleosis-like syndrome, pneumonia, endocarditis, bacterial aortic aneurysm, localized abscesses, papular or pustular cutaneous lesions, conjunctivitis and urethritis.

In the past decade, *L. monocytogenes* has been recognized as a major food-borne pathogen. Outbreaks of listeriosis have been linked to a number of contaminated foods such as coleslaw, Mexican-style soft cheese, pasteurized millk and turkey franks. It has been isolated from fresh produce, dairy products, processed meats and seafood products. About 500 people die each year in the United States from *Listerial* food poisoning; the victims are usually the immunocompromised, pregnant women and neonates.

The isolation and the identification of the bacterium *L. monocytogenes* is a major problem in the monitoring of food hygiene and of medical bacteriology. While a number of putative media for selective culture of *Listeria* spp. have been described in the literature, each have disadvantages. For example, Lovett et al. describe an enrichment broth for selective isolation of *Listeria* spp. and U.S. Pat. No. 6,228,606 describes a method for inhibiting *L. monocytogenes* using a synthetic chromogenic substrate. However, these media detect every species of the genus *Listeria* spp. Thus, supplementary identification tests, such as microscopic, biochemical, immunological, and/or genetic tests must be used to establish the presence of the pathogenic *monocytogenes* species. However, these supplementary manipulations increase the length of time and cost of the analyses, require a vast number of reagents and the use of qualified personnel, and are often a source of error or at least the cause of lower precision and reliability. This is especially true when there is a very small amount of *L. monocytogenes* present.

Other methods for the selective culture of *Listeria* spp. have been described, such as Fraser and Sprerber's medium exploiting the high salt tolerance of *Listeria* spp., and its ability to hydrolyze esculin. Esculin is a glucoside (6-(beta-D-glucopyranosyloxy)-7-hydroxy-2H-1-benzopyran-2-one, CAS No. 531-75-9) obtained from *Aesculus hippocastanum* (the horsechestnut) and is characterized by its fine blue fluorescent solutions. In this approach, the beta-glucosidase activity of *Listeria* hydrolyzes esculin. The hydrolysis products, in combination with iron salts present in the medium, yield a black pigment that is used as a colorimetric indicator of a positive sample. Donnelly & Baigent developed a modified medium similar to the Fraser & Sprerber broth but lacking the colorimetric indicator. This medium exploits the salt tolerance of *Listeria* spp. in conjunction with several antibiotics to yield a medium selective for the growth of *Listeria*. However, these media slow the overall growth rate of *Listeria* cells to achieve inhibition of competitive micro-flora in the sample being tested. Further, the combination of high salt concentration and antibiotics prevents the growth of certain strains of *Listeria*, most notably *L. ivanovii* and *L. grayi*.

Another complicating aspect of conventional selective media is the presence of acriflavin. Acriflavin is an acridine dye that is an effective inhibitor of competitive gram-positive bacteria such as *Bacillus* spp. Unfortunately, acriflavin not only is a suspected carcinogen but is also a fluorophore that is incorporated into the DNA and proteins of growing cells. Thus, acriflavin causes unwanted fluorescent interference in many fluorescence-based assays, such as enzyme-linked immunosorbent assays (ELISA) and the polymerase chain reaction (PCR). Many commercially available *Listeria* detection products rely upon the use of fluorescent reagents for analyte detection.

Thus, there remains a long-felt and unmet need for a *Listeria*-selective medium that 1) does not appreciably interfere with the growth rate of *Listeria* spp.; 2) does not yield bacterial biomass contaminated with interfering fluorophores; and 3) strongly inhibits the growth of non-*Listeria* organisms.

SUMMARY OF THE INVENTION

The present invention is a culture medium for investigating, isolating, counting and directly identifying pathogenic bacteria of the genus *Listeria*. The medium promotes the growth of *Listeria* spp. while simultaneously inhibiting the growth of non-*Listeria* organisms. Further, the medium does not produce a bacterial biomass contaminated with interfering fluorophores.

The medium or the present invention comprises nitrofurantoin, esculin and lithium chloride and is substantially devoid of acriflavin. In a preferred embodiment, no acriflavin is present. In an alternative embodiment, acriflavin is present in concentrations of about 0.01 g/L or less. The medium also uses much lower concentrations of lithium chloride than the prior art. In a preferred embodiment, lithium chloride is present in concentrations of about 5 g/L or less.

The rapid and accurate identification of *Listeria* spp is just one of the advantages the medium of the present invention. For instance, the medium of the present invention does not require a secondary transfer to another medium. Further, the medium does not fluoresce, and therefore is compatible with ELISA-and PCR-based tests to identify *Listeria* spp. Further still, procedures using the medium of the present invention require no special enrichment procedures or secondary manipulations. Finally, the medium of the present invention can be used to detect *L. monocytogenes* in a host of foods, food products and environmental samples, even in the presence of large populations of other non-*Listeria* organisms.

The complete scope of the invention will appear more fully from the following detailed description of the preferred embodiment of the invention.

DETAILED DESCRIPTION OF THE INVENTION

The selective medium of the present invention promotes and enhances the growth of *Listeria* spp. while simultaneously inhibiting the growth of non-*Listeria* organisms. The medium may be used with any type of food product or environmental sample.

In a preferred embodiment (see PDX-1 in Table 1), the medium comprises tryptone, in a concentration ranging from about 15 to about 25 g/L, with a preferred concentration of about 16 to about 18 g/L, with a further preferred concentration of about 17 g/L; peptone, in a concentration ranging from about 1 to about 5 g/L, with a preferred concentration of about 2 to about 4 g/L, with a further preferred concentration of about 3 g/L; sodium chloride, in a concentration ranging from about 1 to about 10 g/L, with a preferred concentration of about 2.5 to about 7.5 g/L, with a further preferred concentration of about 5 g/L; anhydrous dibasic potassium phosphate, in a concentration ranging from about 1 to about 10 g/L, with a preferred concentration of about 2.5 to about 7.5 g/L, with a further preferred concentration of about 5 g/L; yeast extract, in a concentration ranging from about 1 to about 10 g/L, with a preferred concentration of about 2.5 to about 7.5 g/L, with a further preferred concentration of about 6 g/L; cycloheximide, in a concentration ranging from about 0.01 to 0.1 g/L, with a preferred concentration of about 0.025 to about 0.075 g/L, with a further preferred concentration of about 0.05 g/L; acriflavin, in a concentration ranging from no more than about 0.01; naladixic acid, in a concentration ranging from about 0.01 to about 0.1 g/L, with a preferred concentration of about 0.025 to about 0.075 g/L, with a further preferred concentration of about 0.04 g/L; and esculin, in a concentration ranging from about 0.5 to 5 g/L, with a preferred concentration of about 0.75 to about 2 g/L, with a further preferred concentration of about 1 g/L.

In an especially preferred embodiment (see PDX-2 in Table 1), the selective medium of the present invention comprises tryptone, peptone, sodium chloride, anhydrous dibasic potassium phosphate, yeast extract, cycloheximide, naladixic acid and esculin in the amounts described above but contains no acriflavin. Acriflavin consistently inhibits all of the *Bacillus* spp. but also inhibits the hemolytic activity of *L. monocytogenes*.

The ingredients of the selective medium of the present invention are dissolved in distilled water and autoclaved at approximately 121 psig until sterile, usually about 15 min. After cooling, supplements are added. Preferred supplements include ceftazidime, phosphomycin, polymyxin E, ferric ammonium citrate, lithium chloride and nitrofurantoin (Table 2).

Ceftazidime, phosphomycin, polymyxin E and nitrofurantoin are all antibiotics. Ceftazidime is a third generation cephalosporin, and acts to inhibit cell wall synthesis. Other cephalosporins such as ceftriaxone, moxolactam, cefotaxime, cefpodoxime, ceftizoxime, cefoperazone may also be used. The medium of the present invention preferably contains ceftazidime in a concentration ranging from about 0.04 g/L.

Phosphomycin is an antibiotic principally excreted through the kidney. Several studies have shown its activity against gram-positive and gram-negative organisms (Kestle, Kwan), and its clinical efficiency in the treatment of infections of the respiratory (Bacardi), gastrointestinal (Taylor), and urinogenital (Allona) tracts. The medium of the present invention preferably contains phosphomycin in a concentration of about 0.04 g/L.

Polymyxin E, also known as colistin, (CAS No. 1066-17-7) is frequently used as an oral drug for flora suppression of the gastrointestinal canal. The suppression effect is dose dependent because polymyxin E is moderately inactivated by faecal and food compounds. Polymyxin compounds are derived from various species of the soil bacterium *Bacillus*, and are active against gram-negative bacteria. Polymyxin E acts by disrupting the cell membranes of bacteria, destroying their ability to function as osmotic barriers. The medium of the present invention preferably contains polymyxin E in a concentration of about 0.01 g/L.

Ferric ammonium citrate is an iron-containing salt that is often used in the treatment of some forms of anemia. The present medium uses ferric ammonium citrate as a growth enhancer for *Listeria* spp. A concentration ranging from about 0.1 to about 1.0 g/L of ferric ammonium citrate is used, with a preferred concentration ranging from about 0.025 g/L to about 0.075 g/L, and a further preferred concentration of 0.05 g/L.

Lithium chloride is a salt commonly used in selective growth media because high salinity was believed necessary to control bacterial competitors of *Listeria* spp., such as *Enterococcus* spp. and *Bacillus* spp. However, the medium of the present invention uses much lower concentrations of lithium chloride than conventional media. Surprisingly, the low levels of salinity remain effective at inhibiting bacterial competitors. For instance, conventional media often contain lithium chloride in concentrations ranging as high as 10 g/L to 15 g/L. However, the medium of the present invention preferably contains a concentration of lithium chloride ranging from about 1 to about 10 g/L, with a preferred concentration ranging from about 2.5 to about 7.5 g/L, with a further preferred concentration of about 5 g/L or less.

Nitrofurantoin is an antibiotic with signifiant anti-microbial activity against many potential gram-positive competitors. Nitrofurantoin has been shown to be effective at concentrations from about one to two orders of magnitude lower than the minimum inhibitory concentration for *Listeria* spp. (Soriano, Safdar). Further, because nitrofurantoin is non-fluorescent, the selective medium of the present invention does not interfere with ELISA-or PCR-based detection protocols. The medium of the present invention preferably contains a concentration of nitrofurantoin ranging from about 0.001 to about 0.01 g/L, with a preferred concentration of about 0.0025 to about 0.0075 g/L, with a further preferred concentration of about 0.006 g/L.

The following Examples illustrate the features of the novel selective medium disclosed and claimed herein. The Examples are included solely to provide a more complete disclosure of the invention and do not limit the scope of the medium disclosed and claimed herein in any fashion.

EXAMPLES

Example 1

TABLE 1

Medium Formulation, Versions PDX-1 and PDX-2.

| Ingredient | PDX-1 (g/L) | PDX-2 (g/L) |
|---|---|---|
| Tryptone | 17.0 | 17.0 |
| Peptone | 3.0 | 3.0 |
| Sodium Chloride | 5.0 | 5.0 |
| Dibasic Potassium Phosphate (anhydrous) | 6.0 | 6.0 |
| Yeast extract | 6.0 | 6.0 |
| Cycloheximide | 0.05 | 0.05 |
| Acriflavin | 0.01 | — |
| Naladixic acid | 0.04 | 0.04 |
| Esculin | 1.0 | 1.0 |

The solid ingredients were dissolved in distilled water and autoclaved at 121 psig for 15 min to sterilize. After cooling, the following supplements were added:

TABLE 2

Supplements.

| Supplement name | PDX-1 | PDX-2 |
|---|---|---|
| Ceftazidime | 0.04 g/L | 0.04 g/L |
| Phosphomycin | 0.04 g/L | 0.04 g/L |
| Polymyxin E | 0.01 g/L | 0.01 g/L |
| Ferric Ammonium Citrate | 0.5 g/L | 0.5 g/L |
| Lithium Chloride* | 5.0 g/L | 5.0 g/L |
| Nitrofurantoin** | — | 0.006 g/L |

*Lithium chloride is exothermic when dissolved in water. Appropriate care must be taken when adding it to the medium.
**Nitrofurantoin is insoluble in water. A 10 mg/mL stock solution was made in sterile DMSO. The nitrofurantoin/DMSO stock solution was then added to the rest of the medium (600 microliters of stock solution/L medium yields 0.006 g/L nitrofurantoin in the final medium). Solid-medium plates were made from the liquid medium by adding 15 g agar per liter of liquid medium, bringing the medium to a boil to dissolve the agar, cooling the solutions, and sterilizing the same.

Example 2

Comparison of Growth Rates of: PDX-1 vs. Fraser Broth

The purpose of this Example is to compare the growth rate of *L. monocytogenes* in Fraser broth versus the growth of *L. monocytogenes* in PDX-1 liquid medium.

Cultures of *L. monocytogenes* (100 microliters of 10-7 dilution; 1/10 serial dilutions on peptone from overnight *L. monocytogenes* culture in tryptone soy broth (TSB)) were added to 3 mL of Fraser broth and 3 mL of PDX-1. Every hour starting at the time of inoculation, 100 microliters of both the PDX-1 medium and Fraser medium were plated on PALCAM plates in duplicate and incubated at 37 C for the enumeration of colonies. (For data on PALCAM plates, see Van Netten). PALCAM plates are available commercially from a number of international suppliers.) The growth rates of *Listeria* spp. on PDX-1 and Fraser broth media are shown in Table 3.

TABLE 3

Growth Rates of PDX-1 compared to Fraser Broth (CFU/0.1 mL)

| | Hour | | | | | |
|---|---|---|---|---|---|---|
| | 0 | 1 | 2 | 3 | 4 | 5 |
| PDX-1 | 65 | 73 | 69 | 72 | 131 | 273 |
| | 67 | 72 | 76 | 100 | 149 | 257 |
| Fraser | 59 | 74 | 66 | 68 | 94 | 70 |
| | 57 | 66 | 81 | 81 | 77 | 100 |

The data show that the *Listeria* spp. in the PDX-1 sample were able to recover from inoculation and start growth faster than the samples grown in Fraser broth. Also of interest is the fact that both sets of samples were inoculated from the same stock and had the same volume of inoculation. Thus the difference in initial cell counts between the two media (65 and 67 for PDX-1; 59 and 57, for Fraser broth) is significant, suggesting that the PDX-1 medium is less stressful to the cells at initial inoculation. In both runs, the *Listeria* displayed greater survivability in the PDX-1 medium as compared to the Fraser broth.

Example 3

Growth of ATCC Cultures on Solid PDX-1, PDX-2, and Modified Oxford Broth

The purpose of this Example was to plate out ATCC cultures of various bacteria, including *Listeria* spp., on solid PDX-1 and PDX-2 media to obtain a record of their respective colony morphologies, as well as to compare these morphologies to those of corresponding colonies grown on conventional media.

A loop of overnight Trypticase Soy Broth (TSB) culture was streaked out on PDX-1, PDX-2, and Oxford broth supplemented with moxalactam. The various primary cultures were obtained from the American Type Culture Collection, Manassas, Virginia. Plates were stored at 37 C and checked at 20 and 40 hours. The results after 20 hours incubation are shown in Table 4.

TABLE 4

Growth of Different Species on Various Solid media After 20 Hr Incubation at 37 C.

| Species | PDX-1 | PDX-2 | Oxford + Mox |
|---|---|---|---|
| S. choleraesuis | − | − | − |
| M. luteus | − | − | − |
| S. aureus | − | − | Regular, round, off-white colonies |
| L. welshimeri | + | + | + |
| L. ivanovii | + | + | + |
| L. grayi | − | − | Area of some discoloration, without any noticeable colonies where the streak started |

TABLE 4-continued

Growth of Different Species on Various Solid media After 20 Hr Incubation at 37 C.

| Species | PDX-1 | PDX-2 | Oxford + Mox |
|---|---|---|---|
| L. seelgreri | − | − | − |
| L. monocytogenes | + | + | + |
| L. innocua | + | + | + |
| E. faecalis | Discoloration without visible colonies at location of start of streak | Discoloration without visible colonies at location of start of streak | Discoloration without visible colonies at location of start of streak |

As can be seen from the data, the medium according to the present invention is highly selective for the growth of *Listeria* spp. and highly inhibitory of the growth of non-*Listeria* species.

It is understood that the invention is not confined to the particular construction and arrangement of parts illustrated and described herein, but embraces such modified forms thereof as come within the scope of the following claims.

REFERENCES

Allona, A. et al. (1977) "Fosfomycin in chronic urinary infections," *Chemotherapy* (Basel) 23(Suppl. 1):267-274.

Al-Zoreky, N. et al, (1990) "Highly Selective Medium for Isolation of *Listeria monocytogenes* from Food" *Appl. Environ. Microbiol.* October:3154-3157.

Bacardi, R. et al. (1977) "Treatment of respiratory infections with fosfomycin," *Chemotherapthy* 23(Suppl. 1):343-347.

Bannerman, E. et al. (1998) "A New Selective Medium for Isolating *Listeria* spp. from Heavily Contaminated Material, "*Appl. Environ. Microbiol.* 165-167.

Blanco, M. et al. (1989) "A Technique for the Direct Identification of Haemolytic-pathogenic *Listeria* on Selective Plating Media," *Letters in Appl. Microbiol.* 125-128.

Cassiday, P. et al. (1989) "Evaluation of Ten Selective Direct Plating Media for Enumeration of *L. monocytogenes* in Hams and Oysters, " *Food Microbiol.* 113-125.

Donnelly, C. & G. Baigent (1986) "Method for flow cytometric detection of *Listeria monocytogenes* in milk," *Appl. Environ. Microbiol.* 52:689-695.

Fraser, J and W. Sprerber (1988) "Rapid detection of *Listeria* in food and environmental samples by Esculin hydrolysis," *J. Food Prot.* 51:726-765.

Kestle, D. and W. Kirby (1970) "Clinical pharmacology and in vitro activity of phosphonomycin," *Antimicrob. Agents Chemother.* 332-337.

Kwan, K. et al. (1971) "Pharmacokinetics of fosphomycin in man" I. Intravenous administration," *J. Pharm. Sci.* 60:678-684.

Lovett, J. D. et al. (1987) "*Listeria monocytogenes* in raw milk: detection, incidence, and pathogenicity," *J. Food Prot.* 50:188-192.

Peterson, M. et al. (1993) "Parameters for Control of *Listeria monocytogenes*in Smoked Fishery Products . . . ," *J. Food Prot.* 56:11:938-943.

Safdar, A. & D. Armstrong (2003) "Antimicrobial activities against 84 *Listeria monocytogenes* isolates from patients with systemic Listeriosis at a comprehensive cancer center (1955-1997)," *J. Clin. Microbiol.* 41:483-485.

Soriano, F. et al. (1995) "Antimicrobial susceptibilities of *Corynebacterium* species and other non-spore forming gram-positive bacilli to 18 antimicrobial agents," *Antimicrob. Agents Chemother.* 39:208-214.

Taylor, C. et al. (1977) "Enteropathogenic *E. coli* gastroenterocolitis in neonates treated with fosfomycin," *Chemotherapy* (Basel) 23(Suppl. 1):310-5314.

Van Netten, P. et al. (1989) "Liquid and Solid Selective Differential Media for the Detection and Enumeration of *L. monocytogenes* and other *Listeria* spp., " *Int. J. of Food Microbiol.* 1215-1217.

What is claimed is:

1. A *Listeria* spp.-selective medium comprising, in combination,
   a. tryptone, in a concentration of about 17.0 g/L;
   b. peptone, in a concentration of about 3.0 g/L;
   c. sodium chloride, in a concentration of about 5.0 g/L,
   d. anhydrous dibasic potassium phosphate, in a concentration of about 6.0 g/L;
   e. yeast extract, in a concentration of about 6.0 g/L;
   f. cycloheximide, in a concentration of about 0.05 g/L;
   g. naladixic acid, in a concentration of about 0.04 g/L;
   h. esculin, in a concentration of about 1.0 g/L;
   i. ceftazidime, in a concentration of about 0.04 g/L;
   j. phosphomycin, in a concentration of about 0.04 g/L;
   k. polymyxin E, in a concentration of about 0.01 g/L;
   l. ferric ammonium citrate, in a concentration of about 0.5 g/L;
   m. lithium chloride, in a concentration of about 5.0 g/L; and
   n. nitrofurantoin, in a concentration of about 0.006 g/L.

2. The medium of claim 1, wherein the medium is substantially devoid of acriflavin.

* * * * *